United States Patent
Arden-Jacob et al.

(10) Patent No.: US 7,935,822 B2
(45) Date of Patent: May 3, 2011

(54) CARBOXAMIDE-SUBSTITUTED DYES FOR ANALYTICAL APPLICATIONS

(75) Inventors: Jutta Arden-Jacob, Zirndorf (DE); Karl-Heinz Drexhage, Siegen (DE); Monika Hamers-Schneider, Freudenberg (DE); Norbert Kemnitzer, Netphen (DE); Alexander Zilles, Mengerschied (DE)

(73) Assignee: ATTO-TEC GmbH, Siegen (DE)

( * ) Notice: Subject to any disclaimer, the term of this patent is extended or adjusted under 35 U.S.C. 154(b) by 925 days.

(21) Appl. No.: 10/539,790

(22) PCT Filed: Dec. 18, 2003

(86) PCT No.: PCT/EP03/14534
§ 371 (c)(1),
(2), (4) Date: Jun. 17, 2005

(87) PCT Pub. No.: WO2004/055117
PCT Pub. Date: Jul. 1, 2004

(65) Prior Publication Data
US 2006/0154251 A1 Jul. 13, 2006

(30) Foreign Application Priority Data
Dec. 18, 2002 (DE) .................. 102 59 374

(51) Int. Cl.
*C09B 57/00* (2006.01)
*C07D 311/82* (2006.01)
(52) U.S. Cl. .......... 546/48; 546/196; 548/418; 549/384; 549/388; 549/389; 549/394
(58) Field of Classification Search ............. 549/388, 549/394
See application file for complete search history.

(56) References Cited

U.S. PATENT DOCUMENTS

| | | | | |
|---|---|---|---|---|
| 4,647,675 A | * | 3/1987 | Mayer et al. | 549/394 |
| 6,130,101 A | * | 10/2000 | Mao et al. | 436/546 |
| 6,399,392 B1 | * | 6/2002 | Haugland et al. | 436/172 |
| 6,750,357 B1 | * | 6/2004 | Chiarello et al. | 549/394 |
| 7,282,339 B2 | * | 10/2007 | Beechem et al. | 435/7.1 |
| 7,344,701 B2 | * | 3/2008 | Reddington et al. | 424/1.73 |
| 7,365,178 B2 | * | 4/2008 | Campbell et al. | 536/23.1 |
| 7,592,435 B2 | * | 9/2009 | Milton et al. | 536/23.1 |
| 2003/0104380 A1 | * | 6/2003 | Chiarello et al. | 435/6 |
| 2009/0004753 A1 | * | 1/2009 | Antoulinakis et al. | 436/166 |

FOREIGN PATENT DOCUMENTS

| | | |
|---|---|---|
| EP | 0 167 998 | 1/1986 |
| EP | 0 347 697 | 12/1989 |
| GB | 1 407 331 | 9/1975 |
| GB | 1 445 989 | 8/1976 |
| JP | 62-94841 | * 5/1987 |
| JP | 11-302550 | * 11/1999 |
| JP | 2000-118145 | * 4/2000 |
| WO | WO 00/64986 | 11/2000 |
| WO | WO 00/64987 | 11/2000 |
| WO | WO 00/64988 | 11/2000 |
| WO | WO 02/055512 | 7/2002 |
| WO | WO 03/098618 | 11/2003 |

OTHER PUBLICATIONS

Jan Slavik, "Fluorescent Probes in Cellular and Molecular Biology", CRC Press, Boca Raton, Ann Arbor, London, Tokyo, 1994.
K.H. Drexhage, "Structure and Properties of Laser Dyes", in: F.P. Schäfer, Topics in Applied Physics, vol. 1, Dye Lasers, Springer-Verlag, Berlin, Heidelberg, New York, 1973.

* cited by examiner

*Primary Examiner* — Fiona T Powers
(74) *Attorney, Agent, or Firm* — Ursula B. Day; Henry M. Feiereisen

(57) ABSTRACT

The present invention relates to carboxamide-substituted dyes, the production and use of such dyes as labeling groups in analytics.

13 Claims, 18 Drawing Sheets

Fluorene derivatives from naphthalic anhydride from cyclohexanedicarboxylic acid anhydrides from pyridinedicarboxylic acid anhydrides from 1,4,5,6,7,7-hexachloro-5-norbornene-2,3-dicarboxylic acid anhydride

Figure 2

Spectral data in ethanol
(s: acidified with 1% trifluoroacetic acid; b: basic with 1% triethylamine)

$\lambda_a$: Absorbance maximum
$\lambda_f$: Fluorescence maximum
$\eta_f$: Fluorescence quantum yield

| | Structure | $\lambda_a$ / nm | $\lambda_f$ / nm | $\eta_f$ / % |
|---|---|---|---|---|
| 1<br>NK 50 | 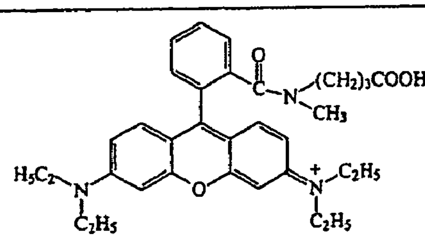 | 561 | 585 | 48 |
| 2<br>NK 51 | 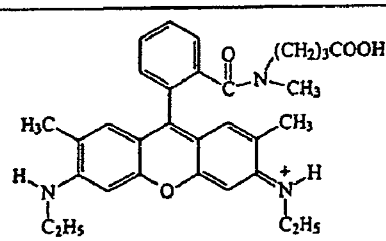 | 536 | 563 | 92 |
| 3<br>NK 54 | 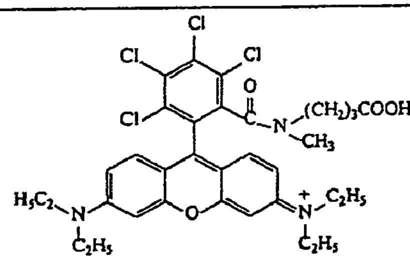 | 584 | 606 | 35 |
| 4<br>NK 56 | 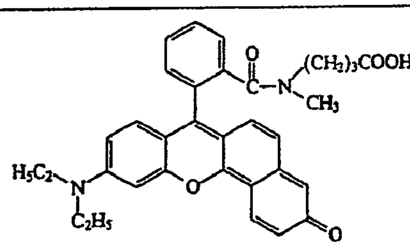 | 566, s<br>622, b | 650, b | 40 |
| 5<br>NK 57 | 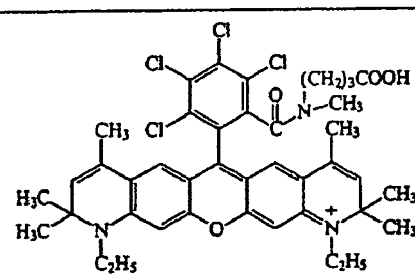 | 624 | 650 | 88 |

Figure 2 (continued)

| | | | | |
|---|---|---|---|---|
| 6 NK 58 | | 562 | 586 | 46 |
| 7 NK 59 | | 535 | 565 | 92 |
| 8 NK 60 | | 584 | 605 | 34 |
| 9 NK 61 | | 625 | 655 | 89 |
| 10 NK 62 | | 565, s 623, b | 650, b | 40 |
| 11 NK 63 | | 615 | 680 | 10 |
| 12 NK 64 | | 614 | 677 | 9 |

Figure 2 (continued)

| | | | | |
|---|---|---|---|---|
| 13 NK 65 | | 618 | 650 | 66 |
| 14 NK 66 | | 618 | 648 | 65 |
| 15 NK 76 | | 563 | 586 | 46 |
| 16 NK 77 | | 561 | 585 | 48 |
| 17 NK 78 | | 619 | 644 | 69 |
| 18 NK 136 | | 512, b | 530, b | 85 |
| 19 NK 106 | | 530 | 556 | 20 |

| | | | | |
|---|---|---|---|---|
| 20 NK 80 |  | 645, b | 700, b | 16 |
| 21 NK 81 |  | 520, b | 545, b | 80 |
| 22 NK 82 |  | 624 | 644 | 89 |
| 23 NK 83 |  | 496 | 519 | 80 |
| 24 NK 107 |  | 552 | - | 0,5 |
| 25 NK 84 |  | 573 | 595 | 92 |

Figure 2 (continued)

| | | | | |
|---|---|---|---|---|
| 26 NK 85 | (rhodamine-type structure with CH₃ groups, N-C₂H₅, xanthene O, bearing o-benzoyl N(CH₃)(CH₂)₃COOH) | 601 | 627 | 88 |
| 27 NK 86 | (thioxanthene rhodamine, N(CH₃)₂ groups, o-benzoyl N(CH₃)(CH₂)₃COOH) | 575 | 600 | 45 |
| 28 NK87 | (selenoxanthene rhodamine, N(CH₃)₂ groups, o-benzoyl N(CH₃)(CH₂)₃COOH) | 580 | - | 0 |
| 29 NK 88 | (fluorescein-like structure, o-benzoyl N(CH₃)(CH₂)₃COOH) | 570, b | - | 0 |
| 30 NK 89 | (triphenylmethane dye, N(C₂H₅)₂ groups, o-benzoyl N(CH₃)(CH₂)₃COOH) | 640 | - | 0 |
| 31 NK 90 | (naphthyl-substituted rhodamine, N(C₂H₅)₂ groups, naphthoyl N(CH₃)(CH₂)₃COOH) | 565 | 590 | 55 |
| 32 NK 108 | (rhodamine with CH₃ and NH-C₂H₅ groups, naphthoyl N(CH₃)(CH₂)₃COOH) | 538 | 560 | 90 |

| | | | | |
|---|---|---|---|---|
| 33 NK 91 |  | 575 | 605 | 35 |
| 34 NK 92 |  | 585 | 615 | 30 |
| 35 NK 109 |  | 562 | 594 | 80 |
| 36 NK 93 |  | 581 | 610 | 30 |
| 37 NK 94 |  | 558 | 580 | 48 |
| 38 NK 95 |  | 558 | 580 | 48 |

| | | | | |
|---|---|---|---|---|
| 39 NK 110 |  | 533 | 560 | 87 |
| 40 NK 96 |  | 570 | 597 | 45 |
| 41 NK 99 |  | 556 | 578 | 35 |
| 42 NK 102 |  | 562 | 590 | 45 |
| 43 NK 103 |  | 562 | 590 | 45 |
| 44 NK 104 |  | 557 | 575 | 1 |

| 45 NK 105 | | 573 | 596 | 92 |

Figure 3

Spectral data in ethanol

λ_a: Absorbance maximum
λ_f: Fluorescence maximum
η_f: Fluorescence quantum yield

| | Structure | $\lambda_a$ / nm | $\lambda_f$ / nm | $\eta_f$ / % |
|---|---|---|---|---|
| 46 NK 47 | | 563 | 588 | 47 |
| 47 NK 48 | | 536 | 565 | 92 |
| 48 NK 52 | | 585 | 607 | 34 |

Figure 3 (continued)

| | | | | |
|---|---|---|---|---|
| 49 NK 53 | | 626 | 648 | 87 |
| 50 NK 55 | | 562, s 623, b | 650, b | 40 |
| 51 NK 67 | | 561 | 585 | 46 |
| 52 NK 68 | | 563 | 585 | 47 |
| 53 NK 70 | | 563 | 584 | 46 |
| 54 NK 71 | | 559 | 583 | 45 |
| 55 NK 97 | | 562 | 586 | 47 |

Figure 3 (continued)

| | | | | |
|---|---|---|---|---|
| 56<br>NK 98 | (rhodamine structure with -C(O)-N(CH₃)(C₁₈H₃₇) amide; xanthene with H₅C₂, C₂H₅ amino groups and +N(C₂H₅)₂) | 563 | 586 | 48 |
| 57<br>NK 100 | (rhodamine structure with -C(O)-N(C₁₀H₂₁)₂ amide) | 562 | 585 | 48 |
| 58<br>NK 101 | (rhodamine structure with -C(O)-N(C₄H₉)(C₂H₄SH) amide) | 562 | 585 | 48 |

| | Structure |
|---|---|
| 59<br>NK 69 | 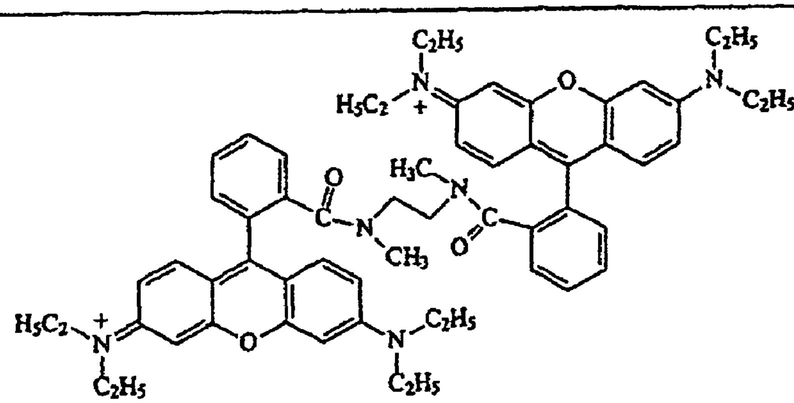 |
| 60<br>NK 72 | 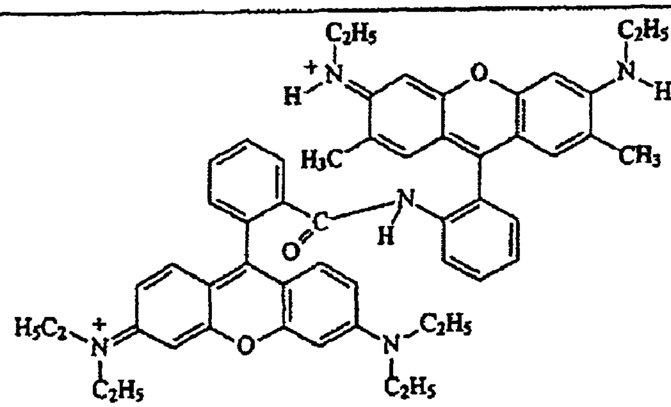 |

NK 51

NK 56

NK 63

NK 65

CARBOXAMIDE-SUBSTITUTED DYES FOR ANALYTICAL APPLICATIONS

BACKGROUND OF THE INVENTION

The present invention relates to carboxamide-substituted dyes, the production and use of such dyes as labeling groups in analytics.

Owing to their very good spectral properties, dyes of the class of xanthene dyes and triphenylmethane dyes and also related derivatives are the preferred labeling groups used in chemical, biological and medical analytics (J. Slavik, Fluorescent Probes in Cellular and Molecular Biology, CRC Press, Boca Raton, Ann Arbor, London, Tokyo, 1994). WO 00/64986 and WO 00/64987 describe dyes of the related classes of carbopyronines and amidopyrylium dyes. In this connection, dyes having a very high fluorescence quantum yield are especially important, since fluorescence enables the labeled analyte to be detected with very high sensitivity. However, nonfluorescent derivatives also gain increasing importance as quenchers in special processes.

The use as labeling groups in processes for detecting analytes requires, aside from simple and reliable detectability, good solubility in various solvents, in particular in aqueous systems. Furthermore, compounds of this kind should be simple and inexpensive to produce and have high stability and good storability.

Many dyes of the abovementioned classes of dye possess a carboxyl group which causes the formation of a colorless lactone, owing to its position and the molecular structure as a function of the solvent environment and the pH, for example even in a neutral or weakly basic solution. In this context, cf. K. H. Drexhage, Structure and Properties of Laser Dyes, in: F. P. Schäfer, Topics in Applied Physics, Vol. 1, Dye Lasers, Springer-Verlag, Berlin, Heidelberg, N.Y., 1973, for example.

The usual covalent coupling, for example via an active ester, of a carboxyl group of this type to the primary amino group of an analyte (peptide etc.) produces an acid amide which rearranges immediately according to the following diagram to give a lactam:

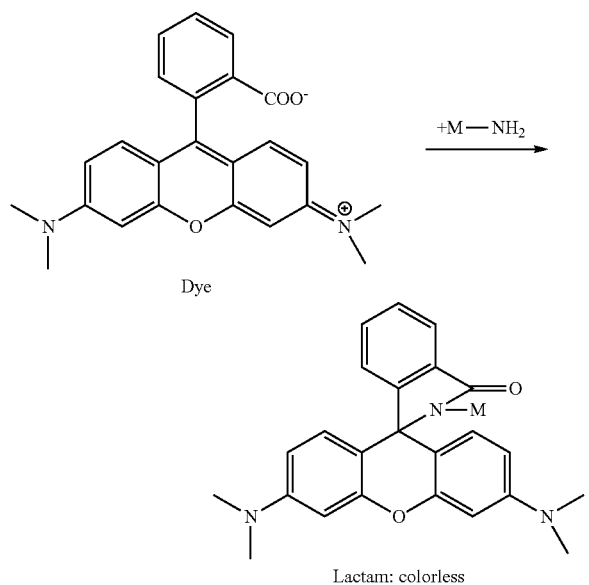

Said lactam, however, is colorless under physiological conditions, thus rendering labeling with the dye unsuccessful, i.e. the labeled analyte cannot be detected by way of absorption and/or fluorescence of the labeling group. Therefore, many known and readily accessible dyes (e.g. rhodamines) are ruled out regarding the use as marker dyes. Previously, this difficulty has been avoided only by introducing additional coupling groups into the dye molecule. However, the precursors required for this are usually difficult to access and require complicated synthesis steps.

WO 02/055512 discloses the preparation of amide derivatives from fluorescein dyes, which comprises first converting the carboxylic acid group at elevated temperatures to give an active ester and then reacting said active ester with a secondary amine in an aqueous solvent mixture. The process according to WO 02/055512 is only applicable to fluorescein and its derivatives and cannot be transferred to other classes of dye. The disclosed process conditions such as temperature and solvents used are in particular not applicable to amino or/and imino group-containing compounds such as, for example, rhodamines. Firstly, the temperatures set for active ester formation result in by- and degradation products, and secondly, the water used as solvent in the reaction of the active ester with an amine can react with said active ester and this in turn results in undesired products.

It is therefore an object of the present invention to modify in a simple manner lactone- or lactam-forming dyes with different functional groups in such a way that they may be used as markers in various fields.

SUMMARY OF THE INVENTION

This object is achieved by providing a carboxamide-substituted dye of the formula (I)

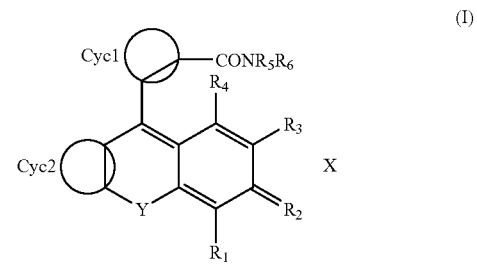

in which

Y=oxygen, sulfur, selenium, $CR_aR_b$, $NR_c$, a direct linkage or is —$R_{14}$ and —$R_{15}$; $R_1$, $R_3$, $R_4$ are independently hydrogen, halogen (such as fluorine, chlorine, bromine, iodine), —$O^{\ominus}$, a hydroxyl group, thiol group, amino group, ammonium group, sulfo group, phospho group, nitro group, carbonyl group (e.g. keto- or aldehyde group), carboxyl group, a carboxylic acid derivative (such as carboxylate, ester, halide, amide, anhydride), a nitrile group, isonitrile group, cyanate group, isocyanate group, thiocyanate group, isothiocyanate group or a straight-chain, branched or cyclic saturated or unsaturated hydrocarbon moiety having up to 40 carbon atoms;

$R_a$, $R_b$, $R_c$ and $R_{14}$, $R_{15}$ independently are as defined for $R_1$, $R_3$, $R_4$;

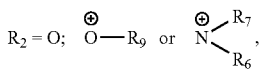

in which
$R_7$, $R_8$, $R_9$ independently are hydrogen or a straight-chain, branched or cyclic saturated or unsaturated hydrocarbon moiety having up to 40 carbon atoms; or
$R_1$ together with $R_2$ is

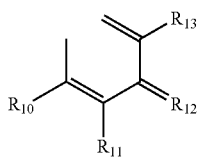

in which
$R_{10}$, $R_{11}$, $R_{13}$ are as defined for $R_1$, $R_3$, $R_4$;

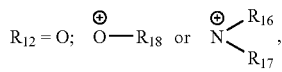

in which
$R_{16}$, $R_{17}$, $R_{18}$ are as defined for $R_7$, $R_8$, $R_9$;
$R_5$, $R_6$, independently are a straight-chain, branched or cyclic saturated or unsaturated hydrocarbon moiety having up to 40 carbon atoms;
Cyc1 is an organic moiety which comprises a ring system selected from aromatic, heteroaromatic, quinoidal and cycloaliphatic rings;
Cyc2 is an organic moiety which comprises a ring system selected from aromatic, heteroaromatic, quinoidal and cycloaliphatic rings;
each of said moieties in the compound according to formula (I) being able to form a ring system with one or more neighboring moieties;
and X being one or more mono- or multivalent anions, when required for balancing the charge;
with the proviso that
Y=oxygen,
Cyc1=phenyl or substituted phenyl,
Cyc2=hydroxyl-, ether- or ester-substituted phenyl
and
$R_2$=O
do not appear in the formula (I) at the same time.
Preference is given to choosing the substituents in the formula (I) in such a way that
Y=oxygen,
Cyc1=phenyl or substituted phenyl,
Cyc2=phenyl or substituted phenyl and

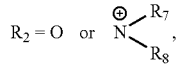

when $R_7$ or/and $R_8$ do not form a ring system with neighboring substituents, do not appear at the same time.

Surprisingly, it was possible to provide differently functionalized dyes according to the formula (I) which have very good spectral properties such as position of the absorption and fluorescence bands, high extinction coefficients and high fluorescence quantum yields and stabilities. The disadvantage of lactone or lactam formation, which occurs in the case of customarily used carboxyl-substituted dyes, is prevented by the generation of secondary amide groups.

Moreover, the properties of the dye were shown to be controllable by the introduction of various moieties at the amide group. Thus it is possible, for example, to increase the lipophilicity of the dye by introducing long alkyl chains as moieties to the amide group. On the other hand, it is possible to increase the hydrophilicity of the dye by introducing, for example, sugar residues or other polar groups. This makes it possible to modulate the properties such as solubility behavior in a simple manner. Furthermore, various linkers may be incorporated at the amide group in order to be able to couple or conjugate the dye via said linkers, for example to an analyte to be detected, such as a peptide or the like.

The hydrocarbon groups comprise according to the invention alkyl groups, alkenyl groups, alkynyl groups, cycloalkyl groups, aryl groups and heteroaryl groups. These groups may contain heteroatoms such as oxygen, sulfur or/and nitrogen. Furthermore, it is possible for other substituents to be bound to said groups, which substituents are preferably selected from among halogen (such as fluorine, chlorine, bromine, iodine), —$O^{\ominus}$, a hydroxyl group, thiol group, amino group, ammonium group, sulfo group, phospho group, nitro group, carbonyl group (e.g. keto- or aldehyde group), carboxyl group, a carboxylic acid derivative (such as carboxylate, ester, carboxylic acid halide, amide, anhydride), a nitrile group, isonitrile group, cyanate group, isocyanate group, thiocyanate group, isothio-cyanate group, imino group, iminium group, alkoxy group, ether group, thioether group and straight-chain, branched or cyclic saturated or unsaturated hydrocarbon groups having up to 40 carbon atoms.

The term "alkyl groups" here comprises straight-chain or branched $C_1$-$C_{40}$-alkyl groups, preferably $C_2$-$C_{35}$-alkyl groups, more preferably $C_5$-$C_{30}$-alkyl groups, still more preferably $C_8$-$C_{20}$-alkyl groups. The alkyl groups are selected, for example, from among methyl, ethyl and straight-chain or branched propyl, butyl, hexyl, decyl, dodecyl and octadecyl groups.

The "alkenyl groups" comprise straight-chain or branched $C_2$-$C_{40}$-alkenyl groups having one or more double bonds at a random position of the hydrocarbon moiety. Depending on the chain length, preference is given to 1-10, 2-8 or 4-6 double bonds per moiety. The alkenyl moieties have 2-40, preferably 4-35, more preferably 8-25, still more preferably 15-20, carbon atoms. Examples of suitable alkenyl groups are ethenyl, propenyl, butenyl, hexenyl, decenyl, dodecenyl and octadecenyl.

Accordingly, the straight-chain or branched alkynyl moieties contain one or more triple bonds at a random position of the hydrocarbon moiety. Depending on the chain length, preference is given to 1-10, 2-8 or 4-6 triple bonds per moieties. The alkynyl moieties have 2-40, preferably 4-35, more preferably 8-25, still more preferably 15-20, carbon atoms. Examples of suitable alkynyl groups are ethynyl, propynyl, butynyl, hexynyl, decynyl, dodecynyl and octadecynyl.

The cycloalkyl groups may be saturated or unsaturated, i.e. they may optionally have one or more double or/and triple bonds. Preference is given to $C_3$-$C_{40}$-cycloalkyl groups, more preferably $C_3$-$C_{20}$-cycloalkyl groups, still more preferably $C_4$-$C_{12}$-cycloalkyl groups, still more preferably $C_5$- or $C_6$-cycloalkyl groups. Suitable cycloalkyl groups are in particular selected from among cyclopropyl, cyclobutyl, cyclopentyl, cyclopentenyl, cyclohexyl, cyclohexenyl, cyclohexadienyl and cyclooctyl. Furthermore, the $C_3$-$C_{40}$-cycloalkyl groups may be bridged and form bicyclic or polycyclic compounds. Examples of polycyclic moieties are norbornane, norbornene and bicyclo[3.2.2]octyl moieties and the particular substituted derivatives thereof. The cycloalkyl groups moreover comprise aliphatic heterocycles such as, for example, tetrahydropyrrole groups, piperidine groups, dioxane groups, tetrahydrofuran groups.

Preferred aryl moieties are $C_3$-$C_{40}$-aryl groups, more preferably $C_6$-$C_{20}$-aryl groups and $C_{10}$-$C_{14}$-aryl groups. Examples of suitable aryl groups are phenyl groups, naphthyl groups, anthracene groups and phenanthrene groups.

The heteroaryl groups are aromatic moieties having 3-40 carbon atoms and one or more heteroatoms, the latter being selected from among oxygen, sulfur and nitrogen. The heteroaryl groups preferably comprise 1-10, preferably 2-6, more preferably 3-5 heteroatoms. The heteroaryl groups contain 3-40, in particular 3-18, more preferably 4-14, still more preferably 5-8, carbon atoms. Examples of suitable heteroaryl groups are pyrrole groups, pyridine groups, pyrimidine groups, indole groups, furan groups, thiophene groups and thiazole groups.

Examples of hydrocarbon groups containing heteroatoms are heteroatom-containing alkyl groups, for example straight-chain or branched $C_1$-$C_{40}$-alkoxy groups, preferably $C_1$-$C_{18}$-alkoxy groups, more preferably $C_2$-$C_{14}$-alkoxy groups, still more preferably $C_6$-$C_{12}$-alkoxy groups. Examples of suitable alkoxy groups are methoxy, ethoxy, straight-chain or branched propoxy, butoxy, decoxy and undecoxy.

Examples of heteroatom-containing aryl groups are aryloxy groups, such as, for example, phenoxy and naphthoxy.

Heteroatom-containing hydrocarbon moieties according to the present invention comprise furthermore, for example, carbonyl groups (such as keto- or aldehyde groups), carboxylic acids, carboxylic acid derivatives (such as halides, esters, amides, anhydrides, carboxylates), ethers, thioethers and alkoxycarbonyl groups, which correspondingly contain 1-40 carbon atoms, preferably 2-35, more preferably 5-30 and also preferably 8-20, carbon atoms.

According to the invention, it is also possible for Cyc1 and Cyc2 to be additionally substituted, the substituents being preferably selected from among halogen (such as fluorine, chlorine, bromine, iodine), —O$^\ominus$, a hydroxyl group, thiol group, amino group, ammonium group, sulfo group, phospho group, nitro group, carbonyl group (e.g. keto- or aldehyde group), carboxyl group, a carboxylic acid derivative (such as carboxylate, ester, halide, amide, anhydride), a nitrile group, isonitrile group, cyanate group, thiocyanate group, isocyanate group, isothiocyanate group, imino group, iminium group or a straight-chain, branched or cyclic unsaturated or saturated hydrocarbon group as defined above, with optionally one or more heteroatoms.

Each of the moieties present in the inventive carboxamide-substituted dye of the formula (I) may, optionally form a ring system together with one or more neighboring moieties. Said ring system preferably comprises 5- or/and 6-membered rings. Preference is given to such a ring system being formed by $R_1$ with $R_8$ or/and $R_3$ with $R_7$ or $R_{11}$, with $R_{17}$ or/and $R_{13}$ with $R_{16}$.

The anions which may be required for balancing the charge may be selected from inorganic or/and organic anions such as, for example, halides, sulfates, carbonates, phosphates, sulfites, sulfides, hydroxides, alkoxides, carboxylates, nitrates, nitrites, etc.

The carboxamide-substituted dyes of the formula (I) are preferably dyes in which Cyc2 in the formula (I) is a nitrogen-containing heterocycle or a ring system which is substituted with at least one amino group. Further preference is given here to $R_2$ being

or to $R_2$ forming, together with $R_1$,

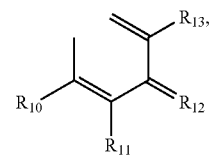

with particular preference being given to $R_{12}$ being

In a preferred embodiment of the present invention, Cyc2 in the formula (I) has any of the structures (A), (B), (C), (D), (E), (F), (G), (H) or (J):

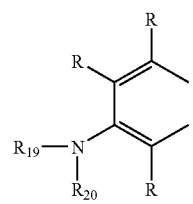

(A)

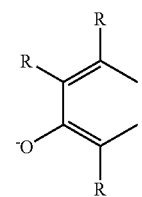

(B)

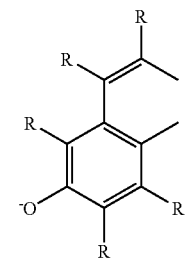

(C)

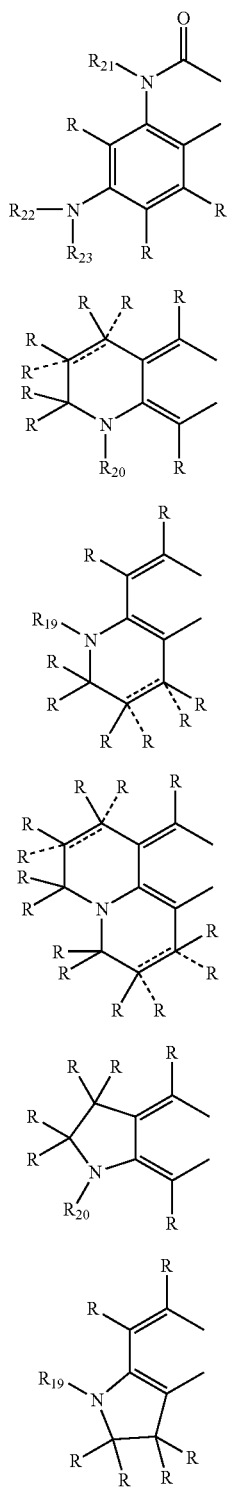

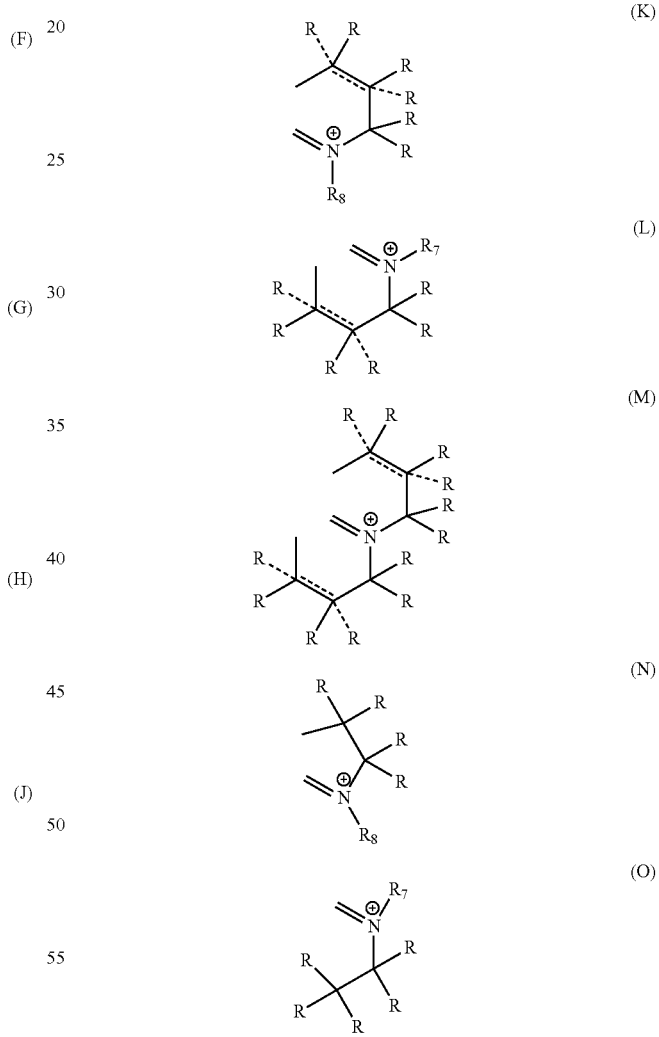

another via single or double bonds. Preference is given to double bonds being located between the linkage sites.

In the structures (A) to (J), neighboring substituents may optionally form further ring systems as defined above. Preference is given here to ring systems which comprise 5- or/and 6-membered rings which may optionally contain further heteroatoms, being formed by the moieties $R_{19}$, $R_{20}$ and $R_{22}$, $R_{23}$ with the in each case neighboring moieties R. Particular preference is given to Cyc2 having any of the structures (A), (D), (E), (F), (G), (H) or (J).

The ring systems formed starting from $R_7$ or $R_8$ together with neighboring substituents preferably result in the following systems (K), (L), (M), (N) or (O):

in which R in each case independently is defined as $R_1$, $R_3$, $R_4$; $R_{19}$, $R_{20}$ and $R_{22}$, $R_{23}$ are independently defined as $R_7$, $R_8$; and
$R_{21}$ is defined as $R_7$ and the dashed lines are optionally double bonds in the presence of which the moieties bound via a dashed line are absent. The substructures (A) to (J) are fused to the remaining ring structure of the formula (I) in such a way that the linkage sites are connected to one in which R in each case independently is defined as $R_1$, $R_3$, $R_4$, and the dashed lines are optionally double bonds, in the presence of which the moieties bound via a dashed line are absent. In the substructures (K) to (O) too, neighboring substituents may form further ring systems as defined above.

In a further preferred embodiment of the present invention $R_2$ in the formula (I) together with $R_1$ is

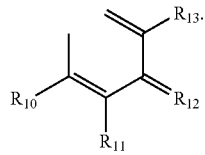

Particular preference is given here to the group of dyes in which $R_{12}$ is oxygen or

Preferred compound classes of the present invention according to formula (I) are depicted by way of the formulae (Ia) to (Ih):

(Ia)

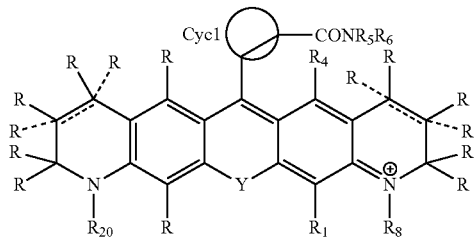

(Ib)

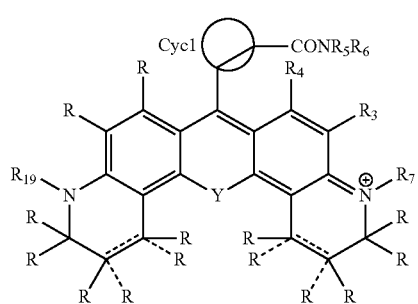

(Ic)

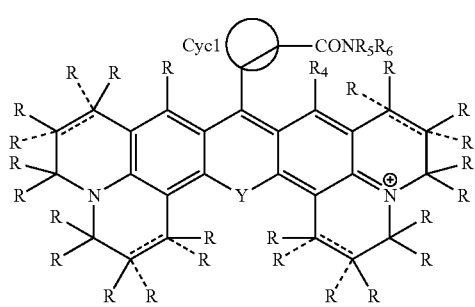

-continued (Id)

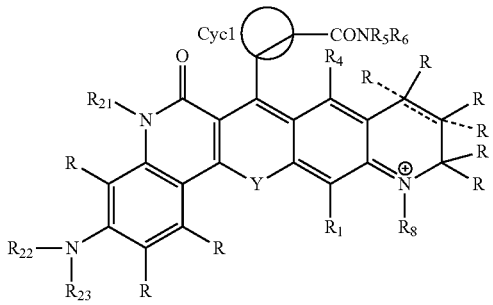

(Ie)

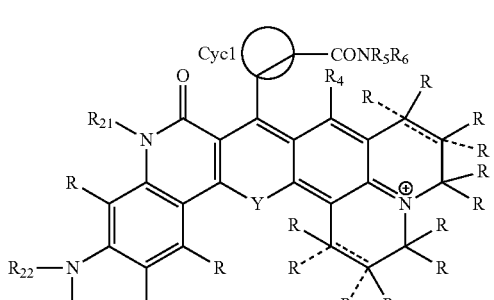

(If)

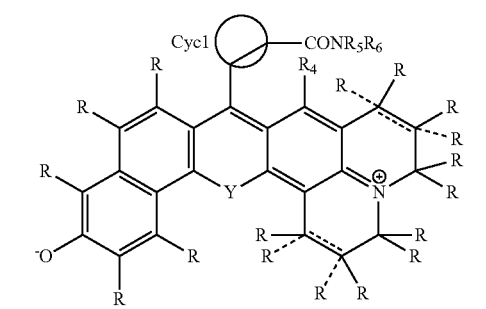

(Ig)

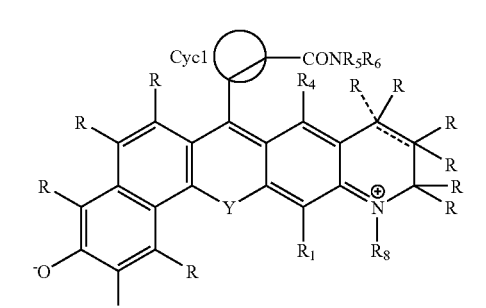

(Ih)

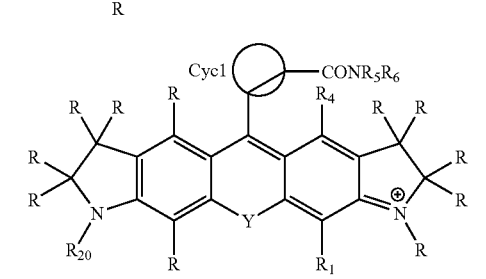

with the moieties being defined as above.

In the compounds of the invention, Cyc1 is optionally a substituted organic moiety which comprises a ring system preferably selected from among substituted and unsubstituted phenyl, naphthyl, pyridyl and cyclohexyl.

In the carboxamide-substituted dyes of the formula (I) of the present invention, the moieties $R_5$ or/and $R_6$ of the carboxamide group preferably have a substituent suitable for coupling to other molecules. Particular preference is given to the possibility of achieving a covalent coupling via such a substituent. Suitable substituents on $R_5$ or/and $R_6$ are a carboxyl group, amino group, hydroxyl group, thiol group, cyano group, halogen group or/and groups having unsaturated units such as, for example, double and triple bonds. It is possible, by means of this functionality, to bind the dyes of the invention to biomolecules or supports, for example.

In a preferred embodiment, at least one of the moieties $R_5$ and $R_6$ is a carboxy-substituted alkyl group, the moiety which is not substituted with a carboxyl group being preferably an alkyl group.

It is moreover possible, by varying the moieties in the inventive carboxamide-substituted dyes of the formula (I), in particular the readily introducible moieties $R_5$ or/and $R_6$, to adjust and modify in a simple manner the properties of the resulting dye molecules with regard to solubility and fluorescence properties.

If $R_5$ or/and $R_6$ carry relatively long alkyl chains, for example (e.g. table 2, compounds 56 and 57), then the lipophilic character increases and the compound is soluble in unpolar media and membranes and may thus be employed, for example, for detecting membrane properties or for measuring molecular distances.

The water solubility of a dye can be improved, for example, when $R_5$ or/and $R_6$ carry, for example, sulfonic or phosphonic acid groups (e.g. table 2, compound 55) or have polyether chains. The latter improve the solubility of the compound also in many organic solvents. Examples of a type of special polyethers are the crown ethers which are used for the fluorescence-sensitive detection of cations and which may also be coupled as aza derivatives to dye molecules by the carboxamide method (e.g. table 2, compound 53).

It is furthermore possible to introduce, for example, sugar residues as $R_5$ or/and $R_6$, thereby making it possible to achieve high solubility in water (see, for example, table 2, compound 51 NK67).

The dyes of the invention moreover achieve the advantage of different meanings of Y enabling the properties of the carboxamide-substituted dyes to be varied, depending on the use purpose. Thus, for example, compounds with Y=selenium have the property of quenching fluorescence. Compounds of this kind are valuable, inter alia, as fluorescence quenchers in bioanalytics.

In contrast, compounds with Y=$CR_aR_b$ result, for example, in a shift to longer wavelengths in the red range, compared to fluorescein or corresponding xanthene dyes such as rhodamines. Such compounds are useful, inter alia, in order to avoid strong background noise during detection, as is produced by customarily used dye derivatives. Examples of such compounds of the invention are the compounds 13 and 14 of table 1 (NK65, NK66).

Dyes which correspond to the formula (I), where Y=—$R_{14}$ and —$R_{15}$, are likewise useful fluorescence quenchers in analytics. Examples of such carboxamide-substituted triphenylmethane dyes are the compounds of the invention 29 and 30 in table 1 (NK88, NK89).

Another aspect of the present invention is a multichromophore system in which a carboxamide-substituted dye according to the formula (I) is coupled via $R_5$ or/and $R_6$ to one or more further dye molecules.

The multichromophore system according to the invention is preferably a system in which a further dye molecule according to the formula (I) is coupled to a carboxamide-substituted dye of the invention. An example of a bichromophore system of this kind is compound 59 in table 3 (NK69).

Preference is given to the coupling to the further carboxamide-substituted dye(s) being carried out in each case via the moiety $R_5$ or/and $R_6$. For example, the nitrogen atoms of the carboxamide group in the dye units are linked via alkyl chains.

A further preferred embodiment of the multichromophore system according to the invention is a bichromophore system of the formula (III).

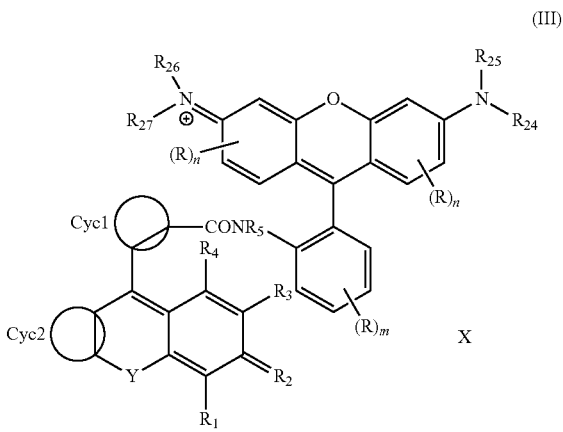

where the moieties are as defined above and $R_{24}$, $R_{25}$ and $R_{26}$, $R_{27}$ are defined as $R_7$, $R_8$, with n independently being 0, 1, 2 or 3 and m being 0, 1, 2, 3 or 4.

An energy transfer (FRET) between the dye molecules takes place in the multichromophore, in particular bichromophore, systems according to the present invention, thereby enabling particular spectroscopic properties to be achieved.

The carboxamide-substituted dyes of the invention distinguish themselves in particular by not displaying the formation of lactones or lactams which occurs in the case of conventional carboxyl group-substituted dyes. The introduction of the carboxamide group also enables the dye molecules to be functionalized in a variable manner, and the latter thus have excellent suitability for a wide variety of applications such as analytical processes. Surprisingly, introduction of the carboxamide group does not substantially alter the very good spectral properties of the starting dyes, i.e. the absorption and fluorescence bands, high extinction coefficients and high fluorescence quantum yields and stability. It was merely observed that the absorption and fluorescence maxima of some dyes undergo a shift to longer wavelengths by 10 nm on average.

It was furthermore found in the context of the present invention that a dye having an appropriate carboxyl group with a tendency to form lactones or lactams (formula (II)) reacts to give the desired inventive carboxamide-substituted dye of the formula (I) by simple reaction of an activated derivative of said dye, previously formed from said carboxyl group, with a secondary amine in common solvents such as acetonitrile or DMF. It is astonishing here that the amide is produced with good yields, even with varying steric and electronic states in the dye precursor. In particular, carboxyl group-containing dyes which differ substantially from fluorescein derivatives regarding the electronic states in the dye molecule were not expected, but were nevertheless able to be successfully converted to the carboxamide-substituted dyes of the invention.

The present invention therefore further relates to a process for preparing carboxamide-substituted dyes of the formula (I), comprising the following steps:
(a) converting the carboxyl group of a dye of the formula (II)

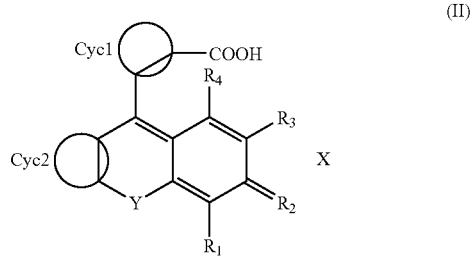

(II)

in which the moieties are defined as indicated above, into an activated form;
(b) reacting the activated dye obtained in step (a) with a secondary amine $HNR_5R_6$; and
(c) optionally isolating the carboxamide-substituted dye of the formula (I) obtained in step (b).

A carboxyl-containing dye according to the formula (II) is preferably activated by converting the carboxyl group into an active ester or an acid chloride. The activation is carried out using common processes well known to the skilled person. In general, the active esters are prepared using customary reagents such as, for example, N-hydroxysuccinimide, N-hydroxyphthalimide, N-hydroxynaphthalimide, O—(N-succinimidyl)-N,N,N',N'-tetramethyluronim tetrafluoroborate (TSTU). Work is preferably carried out at temperatures of from 0° C. to about 60° C., more preferably at 10° C. to 40° C., most preferably at 20° C. to 30° C., in particular at room temperature.

In particular, activated dyes derived from rhodamine are prepared at room temperature in order to avoid decomposition of the rhodamine derivatives. The reaction times vary in this case, depending on the structure of the dye, but the reaction is generally complete after about 5-48 hours, preferably 8-24 hours.

The activated dye obtained in step (a) is reacted with secondary amines which contain the moieties $R_5$ and $R_6$ desired later in the carboxamide-substituted dye of the formula (I). The reaction is preferably carried out at room temperature up to temperatures of approximately 100° C., preferably at temperatures of from about 50° C. to 90° C., more preferably approximately 60° C. to 80° C. For this purpose, the active ester and the appropriate secondary amine are dissolved in an aprotic solvent such as, for example, acetonitrile, DMF, DMSO etc. and heated (carboxamide process). During synthesis of the carboxamide-substituted dyes derived from rhodamine, which are preferred according to the invention, particular care must be taken that the solvent is anhydrous in order to avoid a reaction with the active ester.

Amide formation is usually complete after several hours. The carboxamide-substituted dye obtained in step (b) is optionally isolated from the reaction mixture by processes well known to the skilled person, such as, for example, extracting, filtering, work-up by column chromatography, distillation etc.

A substantial advantage of the process described is the unlimited applicability to all dyes of the formula (II) which contain in particular a carboxyl group which is in the ortho position or, owing to its position, tends to form lactones. Examples of classes of dye which may be employed are listed in FIG. 1. Especially remarkable here is the fact that it is also possible to successfully convert amino and imino or iminium group-containing dyes such as, for example, rhodamines by means of the process of the invention.

The resulting dyes of the invention are particularly well suited as labeling groups in analytical processes.

The present invention therefore further relates to the use of an inventive carboxamide dye according to the formula (I) for the qualitative or/and quantitative determination of an analyte. The dyes of the invention exhibit very good results, both in chemical and in medical and biological detection processes. The determination may be carried out, for example, in aqueous liquids such as body fluids, for example blood, serum, plasma or urine, wastewater samples or food, using detection processes known to the skilled person. In this context, the process may be carried out both as wet assay, for example in a cuvette, or as dry assay on an appropriate reagent support. Determination of the analytes may be carried out via single reaction or by way of a reaction sequence.

In order to detect an analyte, the carboxamide-substituted dye of the invention is preferably coupled to said analyte or/and a support. In a particularly preferred embodiment of the present invention, the dye is coupled to a component of a detection reagent. Such a component is preferably a universal receptor or an analyte analog. Examples of binding partners of this kind are preferably selected from among peptides, polypeptides, nucleic acids, nucleosides, nucleotides, nucleic acid analogs and haptens.

The detection comprises in particular immunological detection or/and detection by nucleic acid hybridization. The analyte to be detected is preferably selected from among peptides, polypeptides, antibodies, nucleic acids, nucleic acid analogs, haptens, cells, cell components, viruses, viral components, metabolites, hormones, neurotransmitters and medicaments.

Any suitable material may be selected as support, for example porous glass, plastics, ion exchange resins, dextrans, cellulose, cellulose derivatives and hydrophilic polymers.

The present invention further relates to a conjugate of a binding partner with a carboxamide-substituted dye according to formula (I). The binding partner here is preferably selected from among peptides, polypeptides, nucleic acids, nucleosides, nucleotides, nucleic acid analogs and haptens. The conjugates may be used, for example, in nucleic acid hybridization processes or immunochemical processes. Such processes are described, for example, in Sambrook et al., Molecular Cloning, A Laboratory Manual, 1989, Cold Spring Harbor.

Coupling to the analyte to be detected or/and to the component of a detection reagent or/and to the support is preferably carried out via the substituents $R_5$ or/and $R_6$ of the carboxamide-substituted dye of the formula (I). Particularly preferred is the formation of a covalent bond. This is accomplished in particular by means of the active ester method well known to the skilled person. Particularly suitable moieties $R_5$ or $R_6$ for this purpose are carboxyl groups or substituents containing carboxyl groups. Such a carboxyl group is in turn itself activatable and may be used preferably for couplings and conjugate formations of the dye of the invention to analytes, components of detection reagents or supports.

For example, the succinimidyl ester (NHS ester) prepared from the dye NK 50 (compound 1) reacts with benzylamine in acetonitrile to give the corresponding conjugate, with the reaction being complete within 30 minutes, according to HPLC or DC analysis. The reaction with aminoethylmaleimide to give the maleimide derivative is also complete after a few hours. This compound was in turn able to be successfully reacted with N-acetylcysteine. The method described can be used to prepare from the terminal carboxyl group all the common derivatives which are used, for example, for coupling to amino and thiol groups of biomolecules.

Compared with conventional dyes, the carboxamide-substituted dyes of the invention have the advantage that, although they contain an activatable carboxyl group, this group does not have a tendency to form lactones or lactams.

The following figures and examples are intended to illustrate the invention in more detail.

BRIEF DESCRIPTION OF THE DRAWINGS

FIG. 3 indicates further examples of carboxamide-substituted dyes of the invention and their spectral data (absorbance maximum, fluorescence maximum and fluorescence quantum yield).

EXAMPLES

Figure 1:
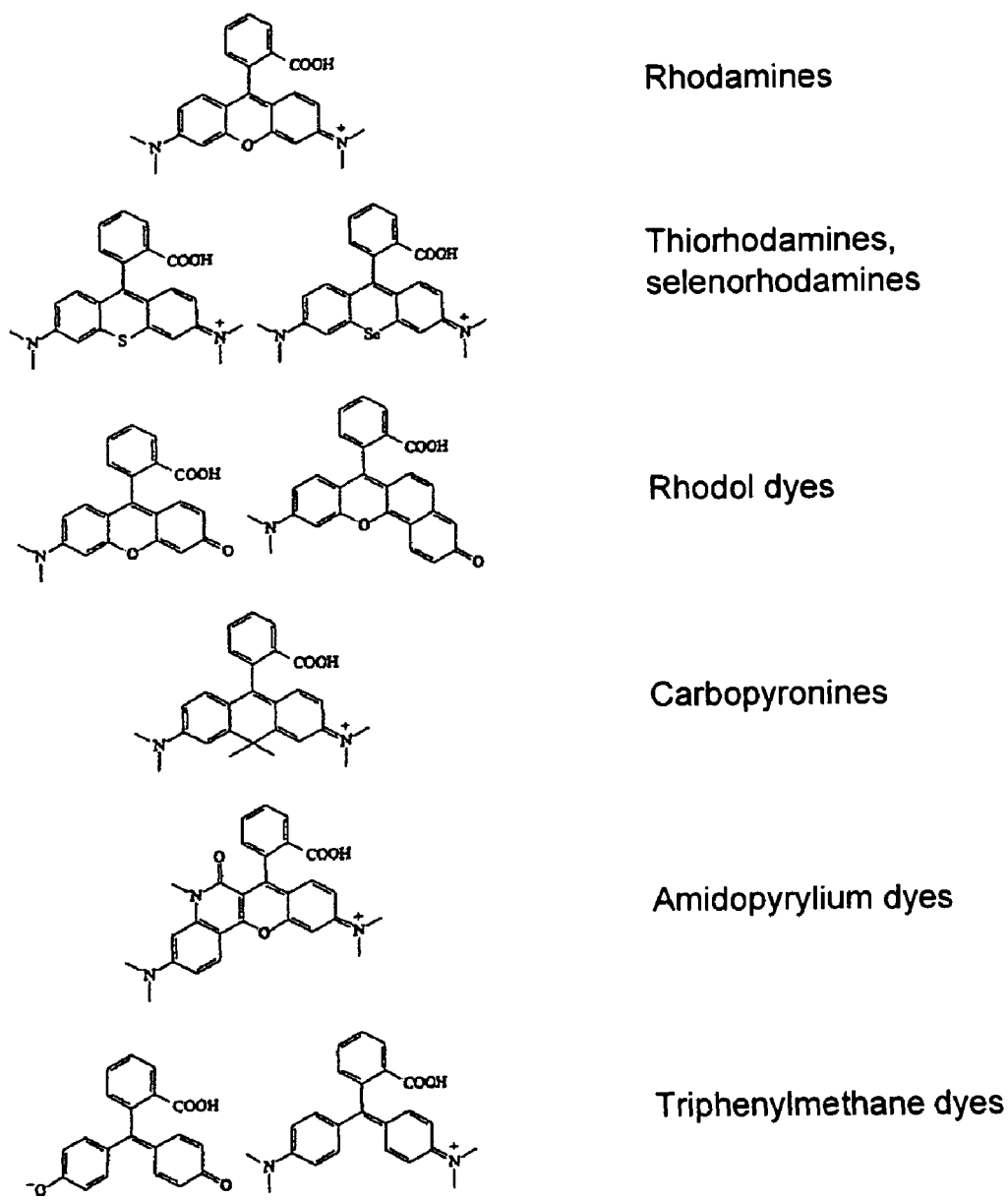
FIG. 1 lists representatives of various carboxyl-containing classes of dye, the substituents having been omitted or not being referred to in any detail.
Figure 1:
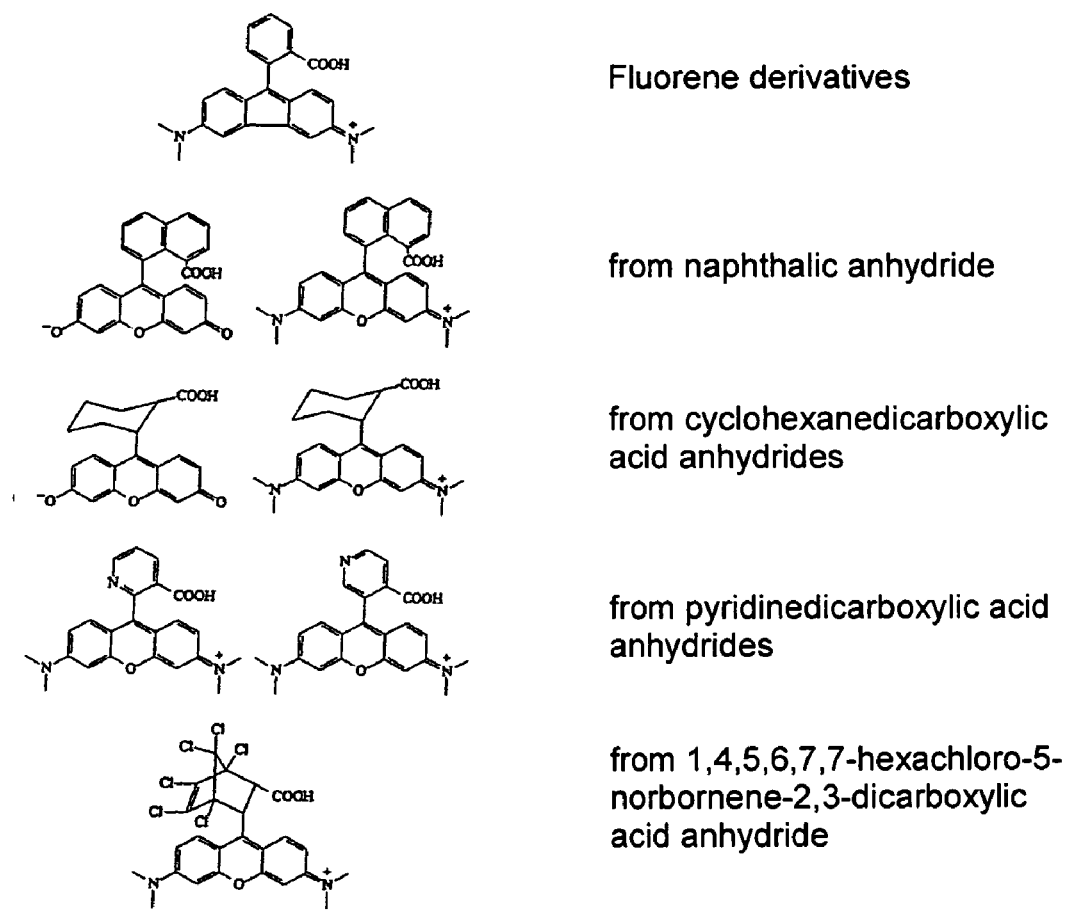
Figure 2:
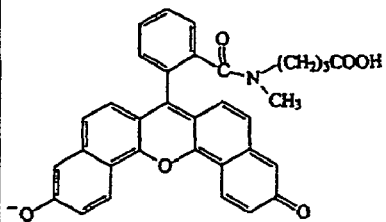
FIG. 2 lists carboxamide-substituted dyes of the invention, having on $R_5$ or $R_6$ a carboxyl group which can be coupled, with the particular spectral data (absorbance maximum, fluorescence maximum and fluorescence quantum yield).
Figure 2:
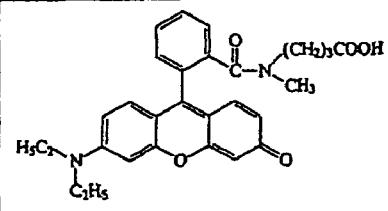
Figure 2:
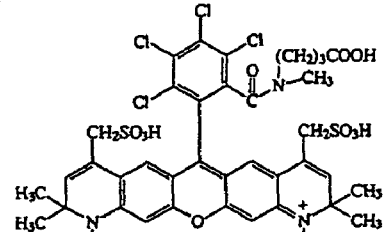
Figure 2:
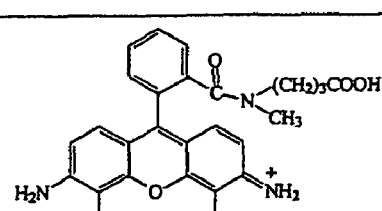
Figure 2:
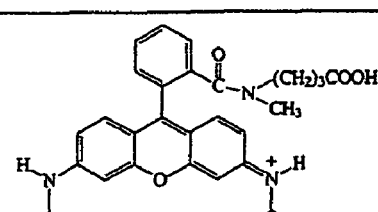
Figure 2:
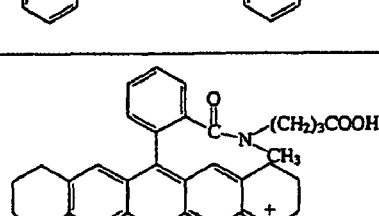
Figure 2:
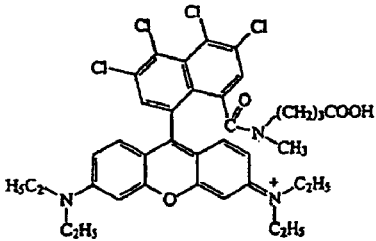
Figure 2:
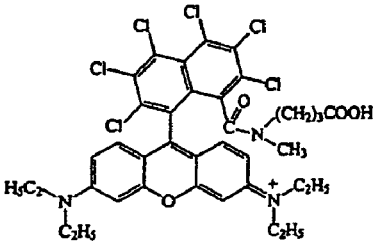
Figure 2:
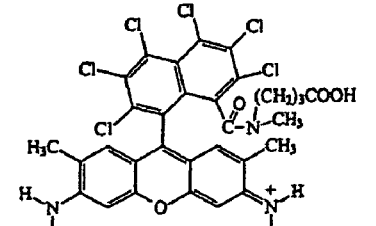
Figure 2:
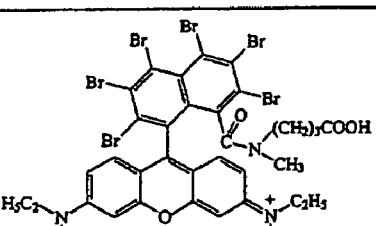
Figure 2:
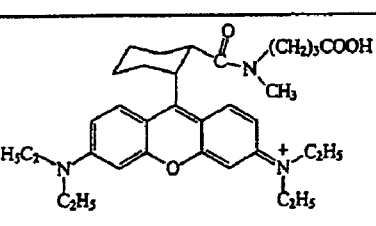
Figure 2:
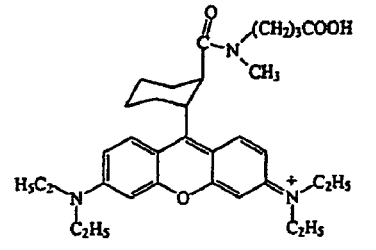
Figure 2:
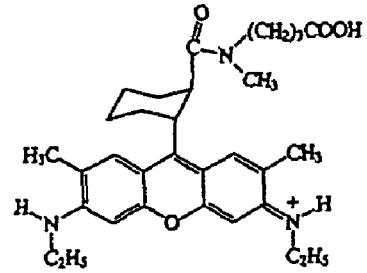
Figure 2:
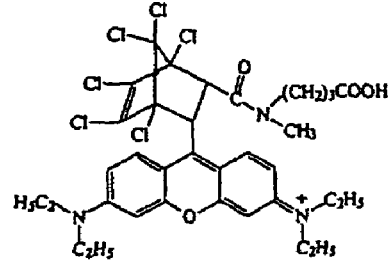
Figure 2:
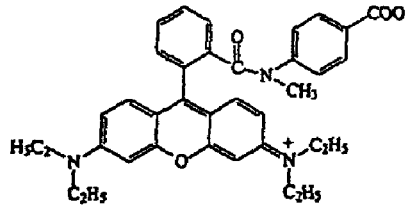
Figure 2:
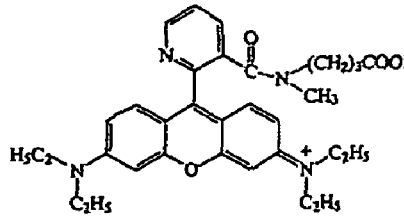
Figure 2:
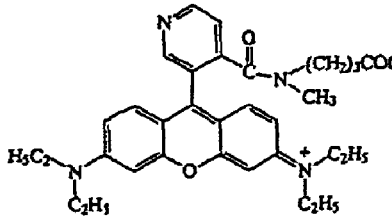
Figure 2:
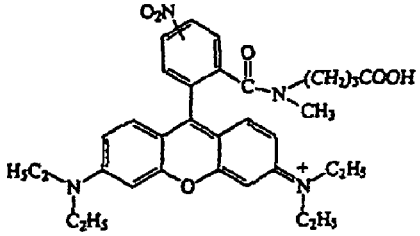
Figure 2:
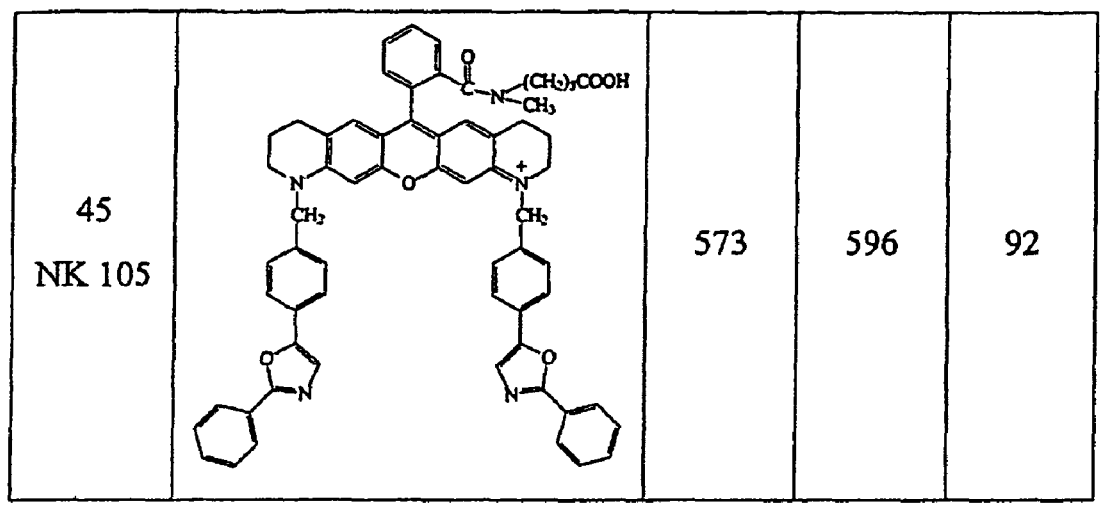
Figure 4:
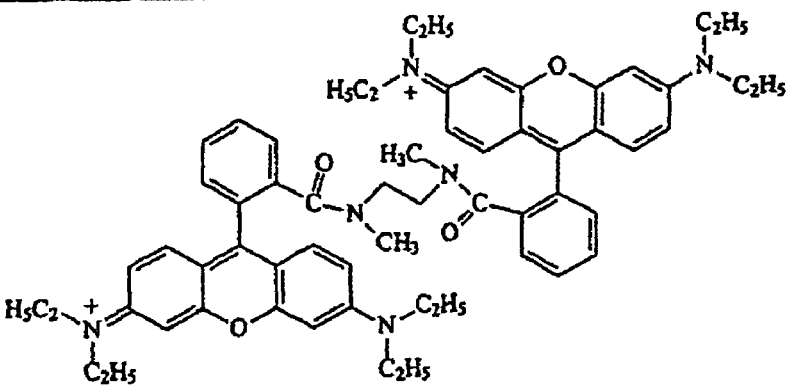
FIG. 4 lists bichromophore systems of the invention.
Figure 4:
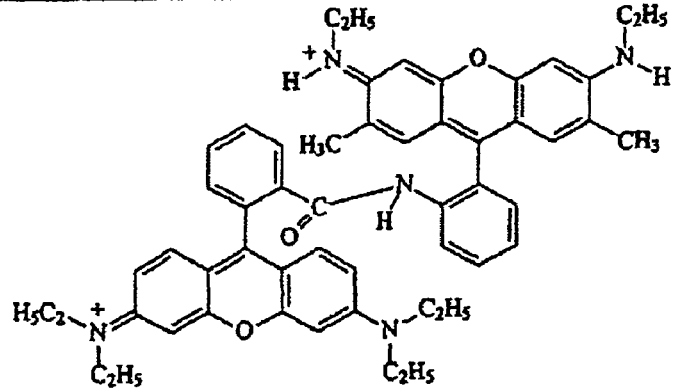
Figure 5:
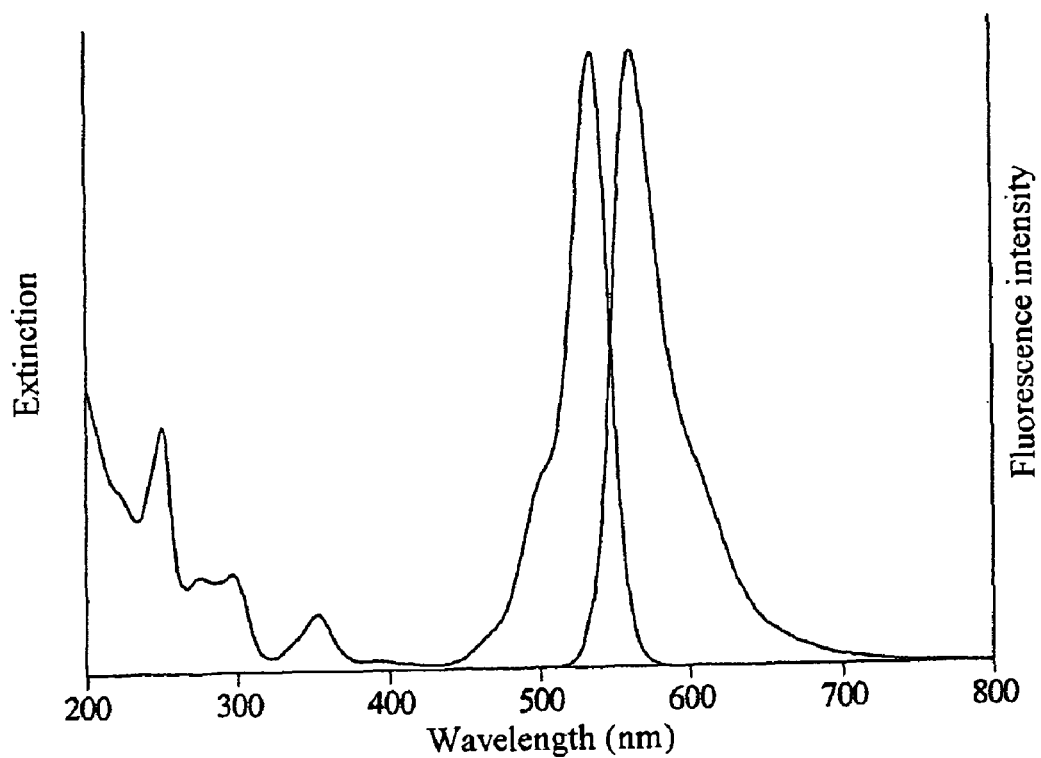
FIG. 5 depicts the absorbance and, respectively, fluorescence spectrum of compound NK51 in ethanol.
Figure 6:
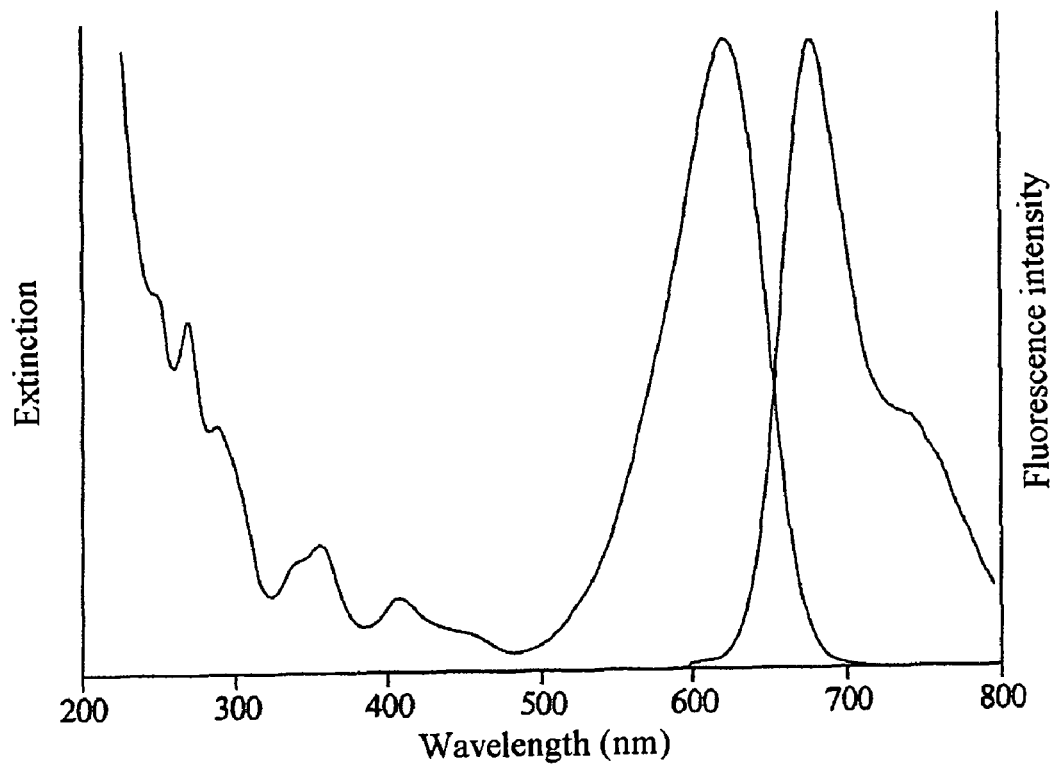
FIG. 6 depicts the absorbance and, respectively, fluorescence spectrum of compound NK56 in ethanol.
Figure 7:
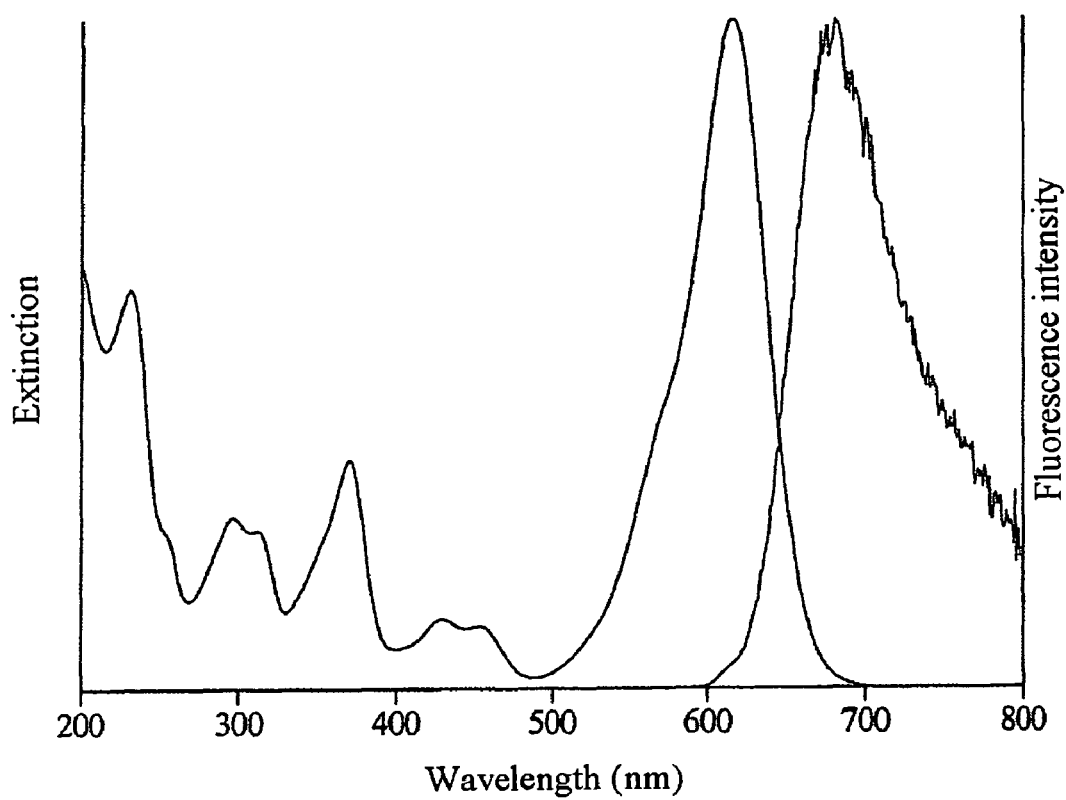
FIG. 7 depicts the absorbance and, respectively, fluorescence spectrum of compound NK63 in ethanol.
Figure 8:
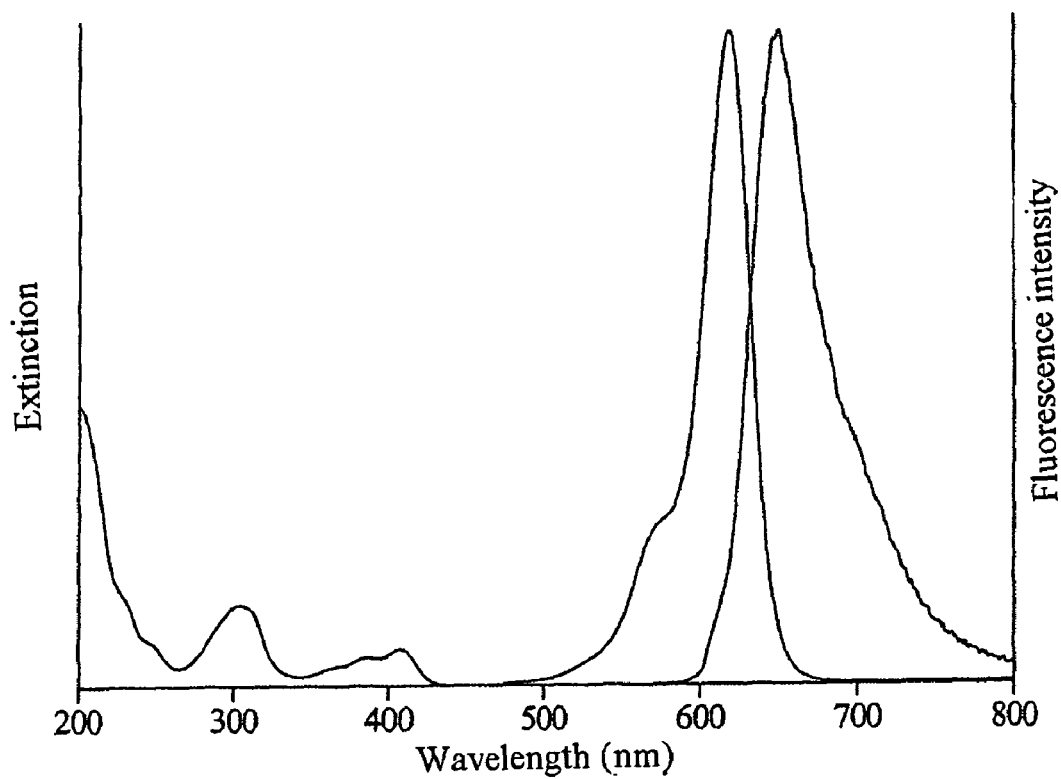
FIG. 8 depicts the absorbance and, respectively, fluorescence spectrum of compound NK65 in ethanol.

The dyes used for the carboxamide process are either commercially available or to be prepared according to syntheses known from the literature or processes known to the skilled person. The secondary amines used are likewise in most cases commercially available or accessible by methods known from the literature. The preferred process for preparing compounds of the invention is described by way of example on the basis of the structures 1 (NK 50), 4 (NK 56), 51 (NK 67) and 18 (NK 79).

Example 1

Preparation of Compounds of the Invention

Compound 1 (NK 50)
Stage 1: Rhodamine B NHS Ester 1 g (2.1 mmol) of commercial rhodamine B (chloride) and 700 mg (2.4 mmol) of O—(N-succinimidyl-N,N,N',N'-tetramethyluronium tetrafluoroborate (TSTU) are taken up together with 700 µl of Hünig base (N-ethyldiisopropylamine) in 50 ml of dry acetonitrile and stirred at room temperature for about two hours and the reaction is monitored by thin-layer chromatography. After the reaction is complete, a little colorless precipitate is removed by filtration and the filtrate is treated with 2 ml of perchloric acid (60% strength). The active ester is precipitated by quickly adding dropwise ice-cold 10% strength sodium perchlorate solution, filtered off with suction, washed with ice water and diethyl ether and finally rigorously dried over phosphorus pentoxide in a desiccator under reduced pressure.

Yield: 0.8 g
ESI mass spectrum: m/z=540.2
Stage 2: NK 50

0.5 g (0.78 mmol) of rhodamine B NHS ester (perchlorate) and 0.25 g (1.56 mmol) of 4-methylaminobutyric acid hydrochloride are suspended in 40 ml of acetonitrile, treated with 270 µl of Hünig base and heated to reflux. The reaction is monitored by thin-layer chromatography and stopped, after the NHS ester has disappeared, usually after four hours. The reaction mixture is evaporated to dryness and purified by column chromatography on neutral aluminum oxide (activity I). The gradient of the eluent is from ethanol to water. The dye fractions are pooled and concentrated in a rotary evaporator. The residue is dissolved in chloroform and extracted by shaking with water saturated with sodium chloride, in order to remove 4-methylaminobutyric acid residues. The chloroform phase is dried and concentrated in a rotary evaporator.

Yield: 0.3 g
$^1$H NMR data in DMSO-$d_6$:
δ 1.2 (T, 12H, —H$_3$); 1.6 (M, 2H, —CH$_2$—); 2.6 (D, 2H, —CH$_2$—); 2.8 (S, 3H, —CH$_3$); 3.1 (D, 2H, —CH$_2$—); 3.6 (Qu, 8H, N—CH$_2$—); 6.9 (S, 2H, ArH); 7.1 (M, 4H, ArH); 7.6 (M, 4H, ArH)
ESI mass spectrum: m/z=542.2

The secondary amide bond formed was shown, on the basis of the dye NK 50 (compound 1), to be stable under the common physiological and experimental conditions. The carboxamide bond is not cleaved at room temperature and a pH of between pH 3 and pH 11 within 24 hours. At an elevated temperature (100° C.), cleavage becomes noticeable only in the pH range above pH 11.

Compound 4 (NK 56)
Stage 1: MR 33 NHS Ester 300 mg (0.69 mmol) of MR 33 are dissolved with 157 mg (0.75 mmol) of dicyclohexylcarbodiimide and 87 mg (0.75 mmol) of N-hydroxysuccinimide in 15 ml of acetonitrile and stirred at room temperature for 24 hours. The reaction mixture is filtered and the filtrate is then treated with diethyl ether. The resultant precipitate is filtered off with suction and dried.

Yield: 80 mg
Stage 2: NK 56

40 mg (0.075 mmol) of MR 33 NHS ester are dissolved together with 25 mg (0.15 mmol) of 4-methylaminobutyric acid hydrochloride and 30 µl of Hünig base in 20 ml of acetonitrile and heated to reflux for about one hour. The reaction is monitored by thin-layer chromatography. After the reaction is complete, the mixture is concentrated to dryness in a rotary evaporator and the residue is purified by column chromatography on silica gel using a gradient from chloroform over ethanol to water.

Compound 51 (NK 67)

0.5 g (0.78 mmol) of rhodamine B NHS ester (perchlorate) and 0.3 g (1.56 mmol) of N-methyl-D-glucamine are dissolved in 20 ml of acetonitrile and heated to reflux. The product is isolated by column chromatography on silica gel with chloroform/ethanol 9:1.

ESI mass spectrum: m/z=620.3
Compound 18 (NK 136)
Stage 1: NK 135

11 g of resorcinol (100 mmol) and 10.8 g of cyclohexanedicarboxylic acid anhydride (isomer mixture, 70 mmol) are mixed, finely ground in a mortar and melted at about 180° C. on an oil bath. The melt solidifies during the reaction. The reaction is complete after approx. 4 hours. After cooling, the solid is crushed in a mortar and extracted in boiling water, filtered off with suction and thoroughly washed with water.

The crude product can be used for the next stage without purification. For further purification, the product may be dissolved in diluted sodium hydroxide solution and reprecipitated with semi-concentrated sulfuric acid.

Stage 2: NK 135 NHS Ester 100 mg (0.3 mmol) of NK 135 are dissolved in 10 ml of acetonitrile with addition of about 100 μl of DMF and 0.5 ml of 20% strength aqueous tetraethylammonium hydroxide solution and admixed with 72 mg (0.35 mmol) of dicyclohexylcarbodiimide and 40 mg (0.35 mmol) of N-hydroxysuccinimide. The solution is stirred at room temperature for 12 hours, then concentrated to half the volume at about 40° C. under reduced pressure, filtered, and subsequently a solid is precipitated by adding water. The crude product is filtered off with suction, washed with a little water and dried over phosphorus pentoxide under reduced pressure. The solid also contains unreacted reactant.

Stage 3: NK 136

100 mg of the solid obtained in this way are suspended with 200 mg of 4-methylaminobutyric acid hydrochloride in 10 ml of acetonitrile and heated to reflux with 250 μl of Hünig base for three hours. The reaction solution is concentrated to dryness in a rotary evaporator and isolated by column chromatography on silica gel using a gradient from chloroform to ethanol. The last colored zone contains the desired product.

ESI mass spectrum: m/z=434.1

Example 2

Examples of Conjugate Formation

NK 50 NHS Ester 0.5 g (0.78 mmol) of NK 50 perchlorate are dissolved in 20 ml of dry acetonitrile, admixed with 250 mg (0.85 mmol) of TSTU and 170 μl (1 mmol) of Hünig base and stirred at room temperature. After the reaction is complete, the volume of the solution is reduced to about a quarter under reduced pressure, treated with 1 ml of 60% strength perchloric acid, and the dye is precipitated by adding dropwise 20% sodium perchlorate solution. The solid is filtered off with suction, thoroughly washed with water and diethyl ether and dried over phosphorus pentoxide under reduced pressure using an oil pump.

Yield: 0.4 g

ESI mass spectrum: m/z=639.3

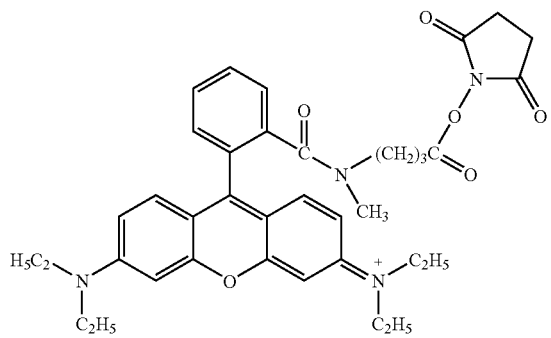

NK 50 aminoethylmaleimide 0.1 mmol of NK 50 NHS ester are dissolved in 5 ml of dry acetonitrile, and admixed with 0.15 mmol of aminoethylmaleimide and 30 μl of Hünig base. The solution is stirred at room temperature for 5 hours, filtered and added dropwise to diethyl ether. The precipitate obtained in this way is dried under reduced pressure using an oil pump.

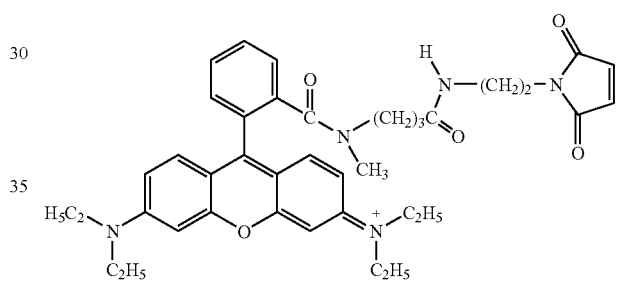

NK 50 aminoethylmaleimide-cysteine conjugate 0.1 mmol of NK 50 aminoethylmaleimide are dissolved in 20 ml of ethanol and admixed in portions with 0.15 mmol of cysteine in total. The mixture is stirred at room temperature and, after about 2 hours, approx. 50 ml of a 10% strength sodium perchlorate solution are added dropwise. The precipitated solid is filtered off and dried over phosphorus pentoxide in a desiccator under reduced pressure.

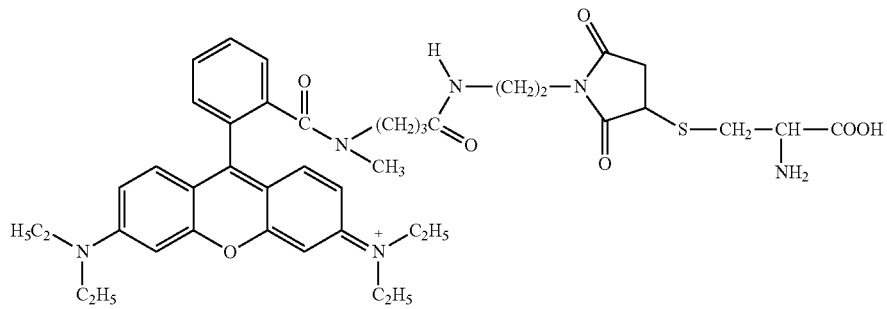

NK 50 dUTP conjugate

10 µmol of 5-(3-aminoallyl)-dUPT are dissolved in 0.5 ml of 0.1 M sodium borate buffer (pH 8) and treated with a solution of 5 µmol of NK 50 active ester in 1 ml of amine-free N,N-dimethylformamide. The solution is stirred at room temperature for 15 hours, the solvent is distilled off under reduced pressure and the residue is purified by chromatography.

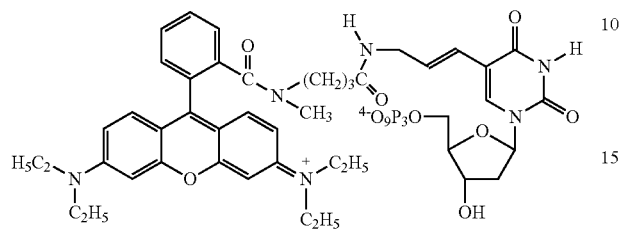

NK 50 digoxin 3-carboxymethyl ether-diaminodioxaoctane conjugate (Dig-CME-DADOO)

0.02 mmol of NK 50 active ester are mixed with 0.02 mmol of Dig-CME-DADOO in acetonitrile with stirring at room temperature for 18 hours. The solution is concentrated and the residue is purified by chromatography.

group, ammonium group, sulfo group, phospho group, nitro group, carbonyl group, carboxyl group, carboxylic acid ester, carboxylic acid halide, carboxylic acid amide, carboxylic acid anhydride a nitrile group, isonitrile group, byanate group, isocyanate group, thiocyanate group, isothiocyanate group or a straight-chain, branched or cyclic saturated or unsaturated hydrocarbon group having up to 40 carbon atoms;

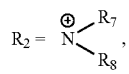

in which $R_7$ and $R_8$, independently are hydrogen or an optionally substituted straight-chain, branched or cyclic saturated or unsaturated hydrocarbon group having up to 40 carbon atoms; or

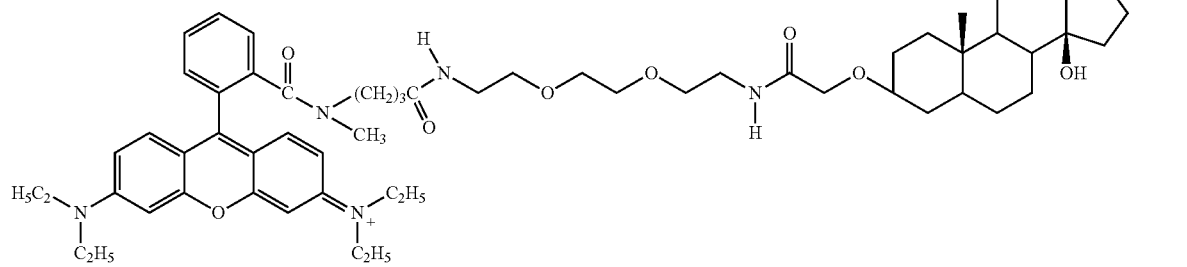

What is claimed is:

1. A carboxamide-substituted dye of the formula (I)

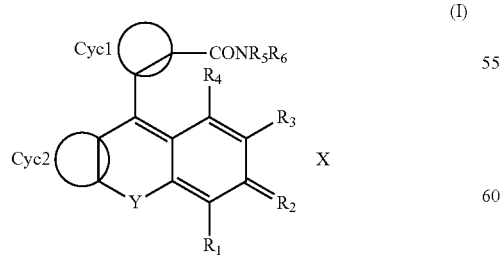

in which

Y=oxygen; $R_1$, $R_3$ and $R_4$ are independently hydrogen, halogen, $-O^{\ominus}$, a hydroxyl group, thiol group, amino $R_1$ together with $R_2$ is

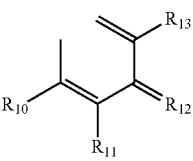

in which $R_{10}$, $R_{11}$ and $R_{13}$ are as defined for $R_1$, $R_3$ and $R_4$;

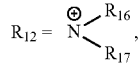

in which $R_{16}$ and $R_{17}$ are as defined for $R_7$ and $R_8$, $R_5$ and $R_6$ independently are a straight-chain, branched or cyclic saturated or unsaturated hydrocarbon group having up to 40 carbon atoms, wherein at least one of $R_5$ and $R_6$ comprises a carboxy group;

Cyc1 is an organic moiety which comprises a ring system selected from aromatic, heteroaromatic, quinoidal and cycloaliphatic rings; wherein Cyc1 is substituted with —CONR$_5$R$_6$ at the ortho-position of the ring attached to a backbone of formula (I);

Cyc2 is an organic moiety which comprises a ring system selected from aromatic, heteroaromatic, quinoidal and cycloaliphatic rings; wherein Cyc2 has a structure selected from (A), (D), (E), (F), (G), (H) or (J),

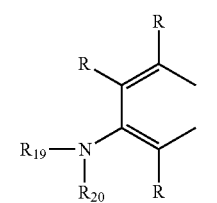
(A)

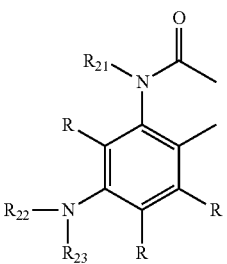
(D)

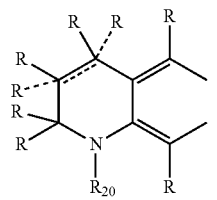
(E)

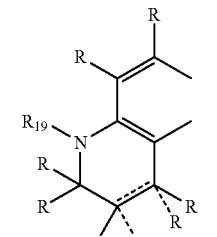
(F)

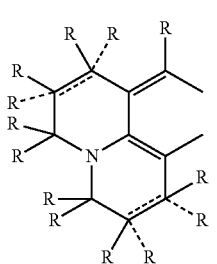
(G)

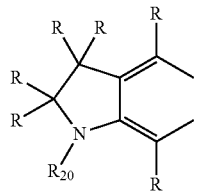
(H)

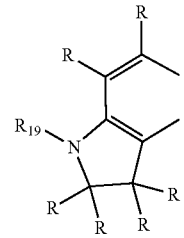
(J)

in which R in each case independently is defined as $R_1$, $R_3$ and $R_4$; $R_{19}$, $R_{20}$ $R_{22}$ and $R_{23}$ are independently defined as $R_7$ and $R_8$; and $R_{21}$ is defined as $R_7$, and the dashed lines are optionally double bonds in the presence of which the moieties bound via a dashed line are absent, each of said moieties in the dye of the formula (I) being able to form a ring system with one or more neighboring moieties;

and X being one or more mono- or multivalent anions, when required for balancing the charge; and wherein at least one of $R_1$, $R_3$, $R_4$, $R_{10}$, $R_{11}$, $R_{13}$ and R is a sulfo group.

2. The carboxamide-substituted dye as claimed in claim 1, in which Cyc1 is substituted or unsubstituted phenyl, naphthyl, pyridyl or cyclohexyl.

3. The carboxamide-substituted dye as claimed in claim 1 in which $R_1$ is bridged with $R_8$ or $R_3$ is bridged with $R_7$ or $R_1$ is bridged with $R_8$ and $R_3$ is bridged with $R_7$ forming a ring system.

4. The carboxamide-substituted dye as claimed in claim 3, in which the ring system comprises 5- or 6-membered rings.

5. The carboxamide-substituted dye as claimed in claim 4, in which a ring system of the structure (K), (L), (M), (N) or (O) is formed:

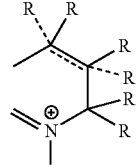
(K)

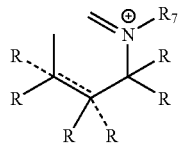
(L)

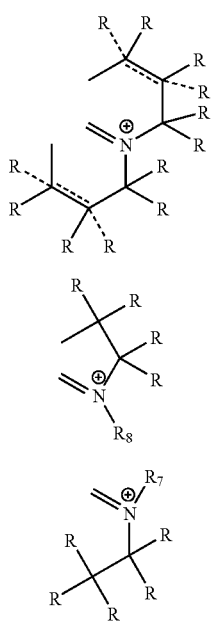

in which R in each case independently is defined as $R_1$, $R_3$ and $R_4$ and the dashed lines are optionally double bonds in the presence of which the moieties bound via a dashed line are absent.

6. The carboxamide-substituted dye as claimed in claim 5, in which Cyc1 is optionally substituted phenyl, Cyc2 has the structure (E), Y=oxygen and $R_7$ and $R_3$ form a ring system (K).

7. A process for preparing carboxamide-substituted dyes of the formula (I) as claimed in claim 1, comprising the following steps:
(a) converting the carboxyl group of a dye of the formula (II)

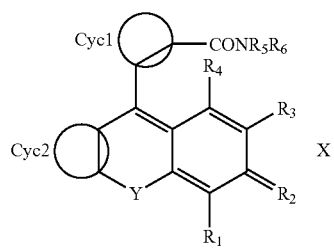

in which the moieties are defined as indicated in claim 1, into an activated form;
(b) reacting the activated dye obtained in step (a) with a secondary amine $HNR_5R_6$; and
(c) optionally isolating the carboxamide-substituted dye of the formula (I) obtained in step (b).

8. The process as claimed in claim 7, in which step (a) is carried out at temperatures of from room temperature to 60° C.

9. The process as claimed in claim 7, in which an aprotic solvent is used in step (b).

10. The process as claimed in claim 7 in which N-hydroxysuccinimide, N-hydroxyphthalimide, N-hydroxynaphthalimide, or O-(N-succinimidyl)-N,N,N',N'-tetramethyluronium tetrafluoroborate (TSTU) are used for activation.

11. The carboxamide-substituted dye of the formula (I) of claim 1, wherein $R_7$ and $R_8$ independently are straight-chained saturated hydrocarbon groups.

12. A carboxamide-substituted dye of the formula (Ia)

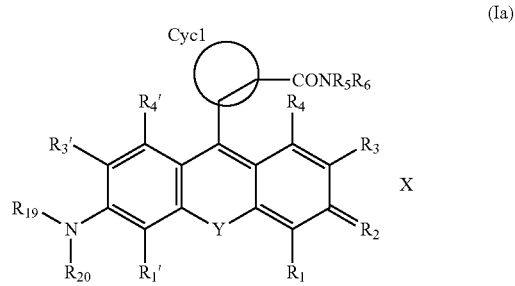

in which
Y=oxygen; $R_1$, $R_1'$, $R_3$, $R_3'$, $R_4$ and $R_4'$ are independently hydrogen, halogen, $-O^\ominus$, a hydroxyl group, thiol group, amino group, ammonium group, sulfo group, phospho group, nitro group, carbonyl group, carboxyl group, carboxylic acid ester, carboxylic acid halide, carboxylic acid amide, carboxylic acid anhydride, a nitrile group, isonitrile group, cyanate group, isocyanate group, thiocyanate group, isothiocyanate group or a straight-chain, branched or cyclic saturated or unsaturated hydrocarbon group having up to 40 carbon atoms; wherein at least one of $R_1$, $R_1'$, $R_3$, $R_3'$, $R_4$ and $R_4'$ is a sulfo group

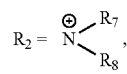

$R_5$ and $R_6$ independently are a straight-chain, branched or cyclic saturated or unsaturated hydrocarbon group having up to 40 carbon atoms; wherein at least one of $R_5$ and $R_6$ comprises a carboxy group,
$R_7$, $R_8$, $R_{19}$ and $R_{20}$ independently are hydrogen or a straight-chain, branched or cyclic saturated or unsaturated hydrocarbon group having up to 40 carbon atoms,
Cyc1 is an organic moiety which comprises a ring system selected from aromatic, heteroaromatic, quinoidal and cycloaliphatic rings; wherein Cyc1 is substituted with $-CONR_5R_6$ at the ortho-position of the ring attached to a backbone of formula (Ia).

13. The carboxamide-substituted dye of the formula (Ia) of claim 12, wherein $R_1$ and $R_1'$ independently are sulfo groups.

* * * * *